United States Patent [19]

Gelbein et al.

[11] 4,443,620

[45] Apr. 17, 1984

[54] PRODUCTION OF EPOXY COMPOUNDS FROM OLEFINIC COMPOUNDS

[75] Inventors: Abraham P. Gelbein, Plainfield; Arthur S. Nislick, Wyckoff, both of N.J.

[73] Assignee: The Lummus Company, Bloomfield, N.J.

[21] Appl. No.: 35,557

[22] Filed: May 3, 1979

[51] Int. Cl.³ .............................................. C07D 301/26
[52] U.S. Cl. .................................... 549/521; 549/520; 549/522
[58] Field of Search ............... 260/348.21, 348.22, 260/348.18, 453 RX; 549/520, 521, 522

[56] References Cited

U.S. PATENT DOCUMENTS

| | | | |
|---|---|---|---|
| 1,938,175 | 12/1933 | Deanesly | 260/453 RX |
| 2,694,722 | 11/1954 | Katz | 260/453 R X |
| 4,008,133 | 2/1977 | Gelbein et al. | 260/348.18 |
| 4,126,526 | 11/1978 | Kwon et al. | 260/348.21 |

FOREIGN PATENT DOCUMENTS 1291328  3/1969  Fed. Rep. of Germany ....................... 260/348.21

*Primary Examiner*—Norma S. Milestone
*Attorney, Agent, or Firm*—Elliot M. Olstein; Louis E. Marn

[57] ABSTRACT

Chlorine and tertiary alkanol dissolved in an inert organic solvent are reacted with calcium oxide in aqueous calcium chloride to produce tertiary alkyl hypochlorite which is recovered in the organic solvent and reacted with water and olefinically unsaturated compound to produce chlorohydrin and tertiary alkanol. Chlorohydrin and tertiary alkanol recovered in the organic solvent are contacted with calcium oxide in aqueous calcium chloride to produce the epoxy compound, and tertiary alkanol recovered in the organic solvent is recycled to hypochlorite production. Calcium chloride produced as by-product in the hypochlorite production and saponification is recovered as an aqueous solution having a calcium chloride concentration of at least 25 wt. % to provide calcium chloride in a usable form.

7 Claims, 1 Drawing Figure

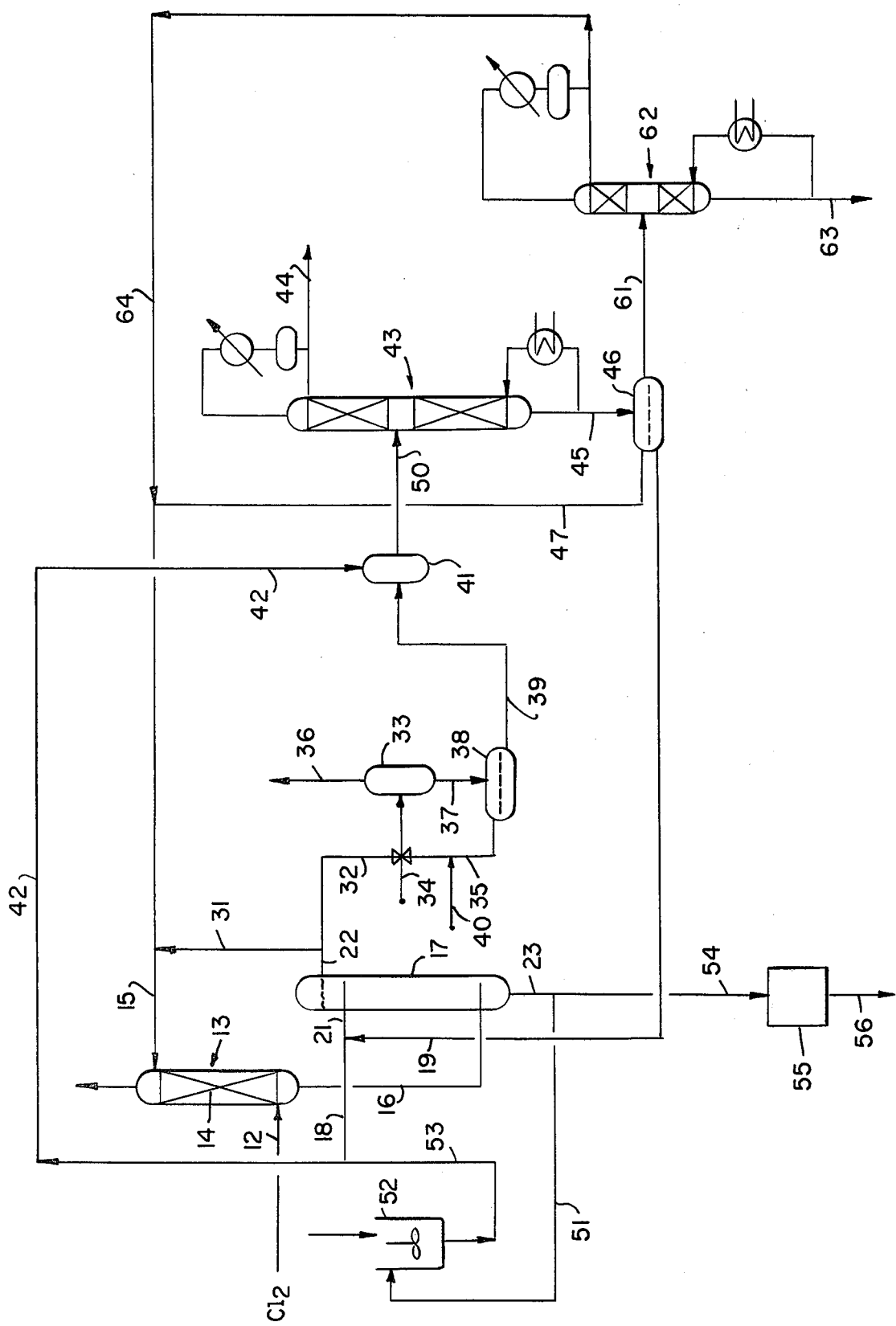

PRODUCTION OF EPOXY COMPOUNDS FROM OLEFINIC COMPOUNDS

This invention relates to the production of epoxy compounds, and more particularly, to a new and improved process for producing epoxy compounds from olefinically unsaturated compounds via the chlorohydrin.

In the production of an epoxy compound, such as propylene oxide, by conversion of propylene to the chlorohydrin, it is known to saponify and neutralize such chlorohydrin by the use of calcium hydroxide. In accordance with such known processes, however, difficulties have been encountered in recovering and disposing of calcium chloride produced as by-product in such process.

In U.S. Pat. No. 4,008,133, there is disclosed a process for producing an epoxy compound from olefinically unsaturated compound, which is integrated with an electrolytic cell for producing chlorine. In accordance with such process, a tertiary alkanol is converted to the corresponding hypochlorite in the presence of caustic cell liquor, with the hypochlorite being subsequently reacted with water and olefin to produce the chlorohydrin, which is then saponified and neutralized with caustic cell liquor. The brine solution produced in the hypochlorite production and saponification is recycled, as electrolyte to the cell. In this manner, the epoxy compound is produced from water and olefin, as net starting materials.

In many cases, however, there may be a high market value for the caustic produced in the cell, whereby it may be more economical to sell such caustic instead of using such for the production of the epoxy compound.

The present invention is directed to a new and improved process for producing an epoxy compound from an olefin, via the chlorohydrin, without the difficulties previously encountered in recovering by-products generated in the process.

In accordance with the present invention, there is provided an improvement in a process for producing an epoxy compound wherein a tertiary alkanol is chlorinated to the tertiary alkyl hypochlorite followed by reacting the hypochlorite with water and olefinically unsaturated compound to produce the chlorohydrin, which is saponified to the epoxy compound, with such improvement resulting from providing the alkali requirement for the hypochlorite production and the saponification as calcium oxide in an aqueous solution of calcium chloride and by employing an inert organic solvent in each of the hypochlorite production, chlorohydrin production, and saponification steps to provide for effective recovery and recycle of tertiary alkanol. In accordance with the present invention, the calcium chloride generated as by-product is recovered as an aqueous calcium chloride solution having a calcium chloride concentration of at least 25%, by weight.

The concentration of the calcium chloride recovered as by-product is determined by the concentration of the combined calcium oxide and calcium chloride employed in the hypochlorite production and saponification. The specific amount of calcium chloride employed is determined in part by the desired concentration of calcium chloride in the byproduct and in part by the solubility of calcium oxide in aqueous calcium chloride. Thus, higher calcium chloride by-product concentrations are favored by higher concentrations of calcium chloride in the solution employed for hypochlorite production and saponification (for example, saturated as to calcium chloride); however, calcium oxide solubility requirements may dictate lower concentrations of calcium chloride; e.g., maximum calcium oxide solubility may occur in a solution having a combined calcium oxide and calcium chloride concentration, equivalent to from 30% to 45%, as calcium chloride. Thus, in general, the combined calcium oxide and calcium chloride has a concentration equivalent to at least 25%, generally at least 30%, all by weight expressed as calcium chloride. The maximum concentration is a saturated solution (about 65 weight percent). In some cases, in order to maximize calcium oxide solubility, the combined concentration may be in the order of 30% to 45%, by weight, expressed as calcium chloride. It is to be understood that such concentrations for the hypochlorite production and saponification may be identical to or different than each other. It is also to be understood that in some cases the calcium oxide may be present in excess of its solubility, e.g., as a partial slurry. The calcium chloride concentration in the byproduct produced in the process (prior to treatment, if any, to further concentrate the calcium chloride) corresponds to the hereinabove noted equivalent calcium chloride concentrations.

In this manner, the calcium chloride by-product is recovered in a concentrated and usable form, thereby eliminating the problems heretofore encountered in the art in attempting to recover calcium chloride by-product resulting from the use of calcium hydroxide in the production of an epoxy compound.

More particularly, chlorine and tertiary alkanol dissolved in an inert organic solvent are reacted with calcium oxide in an aqueous calcium chloride solution. The calcium oxide and calcium chloride is present in the solution in amounts, as hereinabove described. The tertiary alkanol preferably has from 4 to 6 carbon atoms, and most preferably tertiary butanol or tertiary amylalcohol.

In general, the hypochlorite production is conducted at a temperature in the order of from about 5° F. to 220° F., preferably at a temperature from about 32° F. to about 160° F. with the pressure generally being from about 5 psia to 100 psia, preferably from about 10 psia to 50 psia.

In effecting the production of hypochlorite, in order to minimize the amount of free chlorine present in the alkyl hypochlorite introduced as feed to the chlorohydrin production reactor, the hypochlorite production reaction should be effected without a substantial molar excess of chlorine with respect to calcium oxide.

In accordance with the present invention, as a result of providing the calcium oxide to the hypochlorite production in an aqueous calcium chloride solution, the aqueous calcium chloride solution recovered from the hypochlorite production is in a more concentrated form, as hereinabove described, and in some cases may be saturated with calcium chloride at the hypochlorite production conditions. Such aqueous calcium chloride solution may be used as such; for example, as refrigeration brine, road surface treating agent, or may be further concentrated; for example, in an evaporator, and then flaked or spray-dried to produce a powdered product.

The hypochlorite in the organic solvent is then employed for the production of a chlorohydrin by reaction with water and olefinically unsaturated compound.

Such chlorohydrin production may be effected as described in U.S. Pat. No. 4,008,133, which is hereby incorporated by reference. As noted in such patent, the chlorohydrin is preferably contacted with water which is essentially free of chloride ion; i.e., the water should not contain a chloride ion concentration in excess of 1 mole per liter and preferably the chloride ion concentration should not exceed 0.1 mole per liter. Furthermore, as disclosed in the patent, the amount of free chlorine is maintained as low as possible in order to minimize by-product production. Such chlorohydrin production is generally effected at a temperature from about 32° to about 160° F., and preferably at a temperature from about 70° to about 140° F., with the pressure generally being in the order of about 1 psig to 100 psig.

The chlorohydrin production reaction effluent contains water, chlorohydrin, tertiary alkanol, by-products, and organic solvent. The aqueous and organic phases are separated with the aqueous phase being recycled to the chlorohydrin production.

The extraction of organics into the organic phase is favored by elevated temperatures; e.g., 150°–250° F., and by the presence of salt in the aqueous phase. In some cases, salt may be present in the aqueous phase to enhance extraction of organics into the organic phase.

The organic extract is employed as feed to the saponification. In accordance with the present invention, the saponification is conducted by the use of calcium oxide in an aqueous calcium chloride solution. The aqueous calcium chloride solution has a calcium chloride concentration as hereinabove described. In general, such saponification is effected at a temperature from about 150°–250° F., preferably from about 200° to about 230° F., at the autogenous pressure of the system. As a result of such saponification, the chlorohydrin is converted to the epoxy compound, and the hydrogen chloride is neutralized to produce calcium chloride and water. The saponification is preferably effected in combination with a stripping operation to recover the epoxy compound, in crude form, as product.

The saponification effluent is separated into an organic and aqueous phase for recycle to the hypochlorite production, with the organic phase generally initially being employed to dissolve chlorine for introduction into the hypochlorite production reactor. In such a procedure, calcium chloride by-product produced in both the hypochlorite production and the saponification is recovered from the hypochlorite production as an aqueous solution having the hereinabove described concentration.

The organic solvent employed in the process is inert, immiscible with the aqueous phases present in the process, and is a solvent for chlorine as well as hypochlorite, alkanol, and chlorohydrin employed and/or produced in the process. The term "inert" as used herein means that the solvent does not adversely effect the various reactions. As representative examples of such solvents, there may be mentioned: chlorinated hydrocarbons, including chlorinated aromatics, and chlorinated aliphatics (saturated); e.g., chlorobenzene, chlorinated parafins, such as carbon tetrachloride, chloroform, dichloropropane, etc.; chlorinated ethers; and the like. Such solvents may be employed alone or as a mixture of two or more thereof.

The olefinically unsaturated compound employed as feed in the present process may be any one of a wide variety of olefinically unsaturated compounds, including both mono-olefinically and di-olefinically unsaturated compounds. The olefinically unsaturated compounds generally employed as feed are represented by the following structural formula:

wherein $R_1$ and $R_2$ are each separately either hydrogen; alkyl; halo, naphthyl or phenyl substituted alkyl; halo or alkyl substituted phenyl; phenyl; naphthyl; halo or alkyl substituted naphthyl; alkenyl or halo, substituted alkenyl; and $R_1$ and $R_2$ can be linked together to provide a cycloalkene (generally 5 to 10 carbon atoms). The alkyl and alkenyl groups generally contain 1 to 6 carbon atoms and the halo group is preferably iodo-, bromo-, or chloro-, most preferably chloro-. As representative examples of the most suitable feedstocks, there may be mentioned: alkenes having from 2 to 6 carbon atoms, preferably 2 to 4 carbon atoms with ethylene and propylene being particularly preferred; styrene; cyclohexene; stilbene, butadiene; chloroprene; allyl chloride, allyl bromide; bromoprene; cyclohexene, and cyclopentene. The epoxy compounds generally produced in accordance with the invention are represented by the following structural formula:

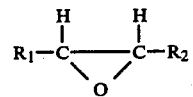

wherein $R_1$ and $R_2$ are as defined above.

The invention will be further described with respect to a preferred embodiment thereof, illustrated in the accompanying drawing wherein:

The drawing is a simplified schematic flow diagram of an embodiment of the process of the present invention.

The preferred embodiment will be particularly described with respect to the production of propylene oxide (1, 2-epoxy propane), but it is to be understood that the embodiment is also applicable to the production of other epoxy compounds.

Referring to the drawing, chlorine in line 12 is introduced into an absorption tower 13, including suitable means for increasing gas-liquid contact, schematically generally indicated as 14, wherein the chlorine is countercurrently contacted with a liquid stream introduced through line 15, which is comprised of tertiary alkanol and tertiary alkyl hypochlorite dissolved in an organic solvent. In particular, the liquid stream contains tertiary butyl alcohol and tertiary butyl hypochlorite dissolved in an organic solvent, e.g., carbon tetrachloride, dichloropropane, or mixtures thereof. The absorption is generally effected at a temperature in the order of from 32° F. to 140° F., and at a pressure in the order of from about 0.5 to about 5.0 atm.

Chlorine dissolved in the liquid, containing tertiary butanol, tertiary butyl hypochlorite and solvent is withdrawn from tower 13 through line 16 and introduced into a hypochlorite production reactor in the form of a tower 17. Calcium oxide slurried in an aqueous solution of calcium chloride, obtained as hereinafter described, in line 18, is combined with a recycle calcium chloride solution, which can contain small amounts of tertiary butyl alcohol, in line 19 and obtained as hereinafter described, and introduced through line 21 into reactor 17 to countercurrently contact the liquid, containing dissolved chlorine, introduced through line 16. As a result of such countercurrent contact, tertiary butanol is converted to tertiary butyl hypochlorite. Reactor 17 is operated at the conditions hereinabove described.

A light organic stream, containing tertiary butyl hypochlorite dissolved in organic solvent is withdrawn from reactor 17 through line 22, and a saturated calcium chloride solution is withdrawn from tower 17 through line 23.

A portion of the calcium chloride solution, in line 23, having a calcium chloride concentration as hereinabove described, is passed through line 51 and introduced into a slurry tank 52 wherein calcium oxide and water is added thereto to provide a slurry of calcium oxide in an aqueous calcium chloride solution for use in the hypochlorite production and saponification of chlorohyrin. The slurry is withdrawn from tank 52 through line 53 and a portion thereof passed through line 18. The remaining portion of the aqueous calcium chloride in line 23 is passed through line 54 for introduction into a zone for purification of brine, schematically indicated as 55. Such purification may be effected as described in U.S. application Ser. No. 851,853, filed on Nov. 16, 1977. The purified calcium chloride solution recovered in line 56 may be further treated to effect concentration and solidification thereof.

A portion of the organics withdrawn from reactor 17 through line 22 may be recycled to absorption tower 13 through line 31 in order to control the concentration of the tertiary hypochlorite present in the feed introduced into the chlorohydrin production reactor and/or provide the required amount of liquid flow for absorbing chlorine in tower 13.

The remaining portion of the hypochlorite dissolved in organic solvent, in line 32, is introduced into a chlorohydrin production reaction zone, schematically generally indicated as 33. Propylene in line 34, as well as recycle water stream in line 35, are also introduced into the chlorohydrin production reaction zone 33. The chlorohydrin production reaction zone 33 may also be provided with a catalyst in order to increase the chlorohydrin production rate. The chlorohydrin production reaction zone 33 is operated at conditions, as hereinabove described.

The chlorohydrin production reactor 33 includes means for effecting mixing of the three phases present in the reactors: namely, a gaseous phase, as well as organic and aqueous liquid phases in order to provide for the chlorohydrin production reaction.

Inert gases, if present, in the reaction feed, such as propane present in a propylene stream obtained from a refinery, are vented from the reaction zone 33 through line 36. A liquid reaction effluent, which contains tertiary butanol, propylene chlorohydrin, as well as any reaction by-products, and which further contains a light aqueous phase, is withdrawn from the reaction zone 33 through line 37 and introduced into a separator, schematically generally indicated as 38, in order to effect separation of an aqueous phase from an organic phase.

An aqueous phase, which primarily contains water, is withdrawn from the separator 38 for recycle to the reactor 33 through line 35. Make-up water may be provided to such recycle stream through line 40.

A heavier organic phase is withdrawn from separator 38 through line 39 and introduced into saponification reactor, schematically generally indicated as 41, which is also provided with a slurry of calcium oxide in an aqueous calcium chloride solution in line 42 to effect saponification of propylene chlorohydrin to propylene oxide. The saponification reactor 41 is operated at the conditions hereinabove described.

The saponification reaction effluent is passed from reactor 41 through line 50 into a fractional distillation column, schematically generally indicated as 43, in order to seaprate from the effluent propylene oxide as well as any light end products; i.e., acetone. Propylene oxide is withdrawn as product through line 44, and may be further treated to effect purification thereof, as required, and known in the art.

A bottoms is withdrawn from distillation column 43 through line 45 and introduced into a separator, schematically generally indicated as 46, in order to effect separation of an aqueous phase from an organic phase. In particular, in separator 46, an aqueous calcium chloride solution, which may contain some minor amounts of tertiary butanol, is recovered through line 19 for recycle to the hypochlorite production reactor 17, as hereinabove described. Any tertiary butanol present in such stream is converted to the hypochlorite in reactor 17.

An organic stream, containing tertiary butanol dissolved in organic solvent is withdrawn from separator 46 through line 47 for introduction into absorption tower 13 for initial dissolution of chlorine and subsequent introduction into reactor 17 for conversion of the tertiary butanol to hypochlorite.

A slip stream of the organic phase may be withdrawn from separator 46 through line 61 and introduced into a fractional distillation column, schematically generally indicated as 62, in order to separate a net heavy organic product therefrom through line 63. An overhead comprised of tertiary butanol in organic solvent is recovered through line 64 for ultimate recycle to the chlorine dissolution step.

It is to be understood that the chlorine employed for production of the hypochlorite may be obtained from an electrolysis cell, with sodium hydroxide and hydrogen also being recovered as product from such cell.

The present invention is particularly advantageous in that it provides an alternative means for producing olefin oxide through the chlorohydrin, which does not require the use of sodium hydroxide, and which permits effective recovery of by-product without the problems heretofore encountered in the art in attempting to recover such by-product. Thus, in accordance with the present invention, by employing a slurry of calcium oxide in an aqueous solution of calcium chloride for both hypochlorite production and saponification, it is possible to recover calcium chloride in a more concentrated form, and in some cases, as a saturated solution thereof.

Numerous modifications and variations of the present invention are possible in light of the above teachings and, therefore, within the scope of the appended claims, the invention may be practiced otherwise than as particularly described.

We claim:

1. A process for converting an olefinically unsaturated compound to the corresponding epoxy compound, comprising:

contacting a tertiary alkanol in an inert organic solvent, chlorine and calcium oxide in aqueous calcium chloride having a combined concentration of calcium oxide and calcium chloride equivalent to at least 25 weight percent expressed as calcium chloride to produce tertiary alkyl hypochlorite and aqueous calcium chloride; recovering tertiary alkyl hypochlorite in the inert organic solvent; contacting tertiary alkyl hypochlorite in the inert organic solvent, water and an olefinically unsaturated compound to produce the corresponding chlorohydrin and a tertiary alkanol; recovering tertiary alkanol and chlorohydrin in the inert organic solvent; contacting chlorohydrin and tertiary alkanol in the inert organic solvent and calcium oxide in an aqueous solution of calcium chloride having a combined concentration of calcium oxide and calcium chloride equivalent to at least 25 weight percent expressed as calcium chloride to convert the chlorohydrin to the corresponding epoxy compound and produce aqueous calcium chloride; recovering said epoxy compound; recovering tertiary alkanol in the inert organic solvent; passing tertiary alkanol in the inert organic solvent to the hypochlorite production; recovering from said hypochlorite production and said epoxy compound production an aqueous solution of calcium chloride having a calcium chloride concentration of at least 25 weight percent; and combining calcium oxide with a portion of said recovered aqueous solution of calcium chloride for providing said calcium oxide in aqueous calcium chloride for the producing of hypochlorite and epoxy compound.

2. The process of claim 1 wherein aqueous calcium chloride from the saponification includes some tertiary alkanol, said aqueous calcium chloride including tertiary alkanol being introduced into the hypochlorite production to convert the tertiary alkanol to tertiary alkyl hypochlorite.

3. The process of claim 2 wherein the tertiary alkanol is tertiary butanol.

4. The process of claim 3 wherein the olefinically unsaturated compound is selected from the group consisting of propylene and allyl chloride.

5. The process of claim 1 wherein the combined calcium oxide and calcium chloride concentration produces aqueous calcium chloride from the hypochlorite and epoxy compound production saturated as to calcium chloride.

6. The process of claim 1 wherein the combined concentration of calcium oxide and calcium chloride is from 30% to 45%, by weight, expressed as calcium chloride.

7. The process of claim 2 wherein a portion of the aqueous solution of calcium chloride recovered from the hypochlorite production is combined with calcium oxide for providing said calcium oxide in aqueous calcium chloride.

* * * * *